US008729301B2

(12) United States Patent
Telgenhoff et al.

(10) Patent No.: US 8,729,301 B2
(45) Date of Patent: May 20, 2014

(54) METHOD OF DEHYDRATING ACETIC ACID

(75) Inventors: Michael David Telgenhoff, Midland, MI (US); Arthur James Tselepis, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 419 days.

(21) Appl. No.: 12/812,823

(22) PCT Filed: Feb. 26, 2009

(86) PCT No.: PCT/US2009/035235
§ 371 (c)(1),
(2), (4) Date: Jul. 14, 2010

(87) PCT Pub. No.: WO2009/123806
PCT Pub. Date: Oct. 8, 2009

(65) Prior Publication Data
US 2011/0166386 A1    Jul. 7, 2011

Related U.S. Application Data

(60) Provisional application No. 61/042,039, filed on Apr. 3, 2008.

(51) Int. Cl.
*C07C 51/42* (2006.01)

(52) U.S. Cl.
USPC ............................................. 562/608

(58) Field of Classification Search
None
See application file for complete search history.

(56) References Cited

U.S. PATENT DOCUMENTS

| 1,917,410 | A | 7/1933 | Webber et al. |
| 2,031,637 | A | 2/1936 | Dreyfus |
| 2,041,668 | A | 5/1936 | Wentworth |
| 2,275,802 | A | 3/1942 | Othmer et al. |
| 2,317,758 | A | 4/1943 | Guinot |
| 2,412,215 | A | 12/1946 | Guinot |
| 2,549,587 | A | 4/1951 | Fiala et al. |
| 3,951,755 | A | 4/1976 | Sartorius et al. |
| 5,160,412 | A | 11/1992 | Berg |
| 5,167,774 | A | 12/1992 | Berg |
| 5,980,696 | A | 11/1999 | Parten et al. |
| 2007/0068792 | A1 | 3/2007 | Jang et al. |

FOREIGN PATENT DOCUMENTS

| CA | 330190 | 2/1933 |
| DE | 877604 | 5/1953 |
| GB | 587269 | 4/1947 |
| GB | 596217 | 12/1947 |
| GB | 623991 | 5/1949 |

OTHER PUBLICATIONS

Chien I. L. et al., Chemical Engineering Science, Oxford, GB, vol. 59, No. 21, Nov. 1, 2004, pp. 4547-4567.*
Lee et al., Journal of Polymer Research vol. 1, No. 3, 247-254, Jul. 1994.*
Hoover et al., J. Am. Chem. Soc., 1961, 83 (16), pp. 3400-3405.*
Database Caplus Chemical Abstracts Service, Columbus, Ohio, US; Database Accession No. 1993:59873, Abstract of EP 509213, Seiler et al., Oct. 21, 1992.*
Chien I. L. et al., "Design and control of acetic acid dehydration system via heterogeneous azeotropic distillation", Chemical Engineering Science, Oxford, GB, vol. 59, No. 21, Nov. 1, 2004, pp. 4547-4567.
Lee et al., "Dehydration of acetic acid/water mixtures by pervaporation with a modified poly(4-methyl-1-pentene) membrane", Journal of Polymer Research, vol. 1, No. 1, Jul. 1994, pp. 247-254.
D. M. Smith et al., "Titrimetric Determination of Water in Organic Liquids Using Acetyl Chloride and Pyridine", J. Am. Chem. Soc., vol. 57, No. 5, May 1935, pp. 841-845.

* cited by examiner

*Primary Examiner* — Karl J Puttlitz
(74) *Attorney, Agent, or Firm* — Howard & Howard Attorneys PLLC

(57) ABSTRACT

The invention pertains to a process for dehydrating wet acetic acid. One embodiment of the invention comprises contacting wet acetic acid with acetyl chloride. Another embodiment of the invention comprises contacting wet acetic acid; acetic anhydride; and a catalytic effective amount of hydrogen chloride, acetyl chloride, or a chlorosilane.

19 Claims, No Drawings

METHOD OF DEHYDRATING ACETIC ACID

CROSS REFERENCE TO RELATED APPLICATIONS

This application is a U.S. national stage filing under 35 U.S.C. §371 of PCT Application No. PCT/US09/35235 filed on Feb. 26, 2009, currently pending, which claims the benefit of U.S. Provisional Patent Application No. 61/042,039 filed Apr. 3, 2008, under 35 U.S.C. §119 (e). PCT Application No. PCT/US09/35235 and U.S. Provisional Patent Application No. 61/042,039 are hereby incorporated by reference.

BACKGROUND OF THE INVENTION

Currently there are at least four commercial ways to manufacture acetic acid. The fermentation of fruit (apples) or wood waste are the oldest. The reaction of acetylene with water to form acetaldehyde followed by air oxidation is still in use. Fermentation of ethanol to acetic acid is used when cheap ethanol is available. The reaction of methanol with carbon monoxide in aqueous solution is favorable when cheap methanol is available. The air oxidation of butane to give a multitude of products, approximately forty, including acetic acid is another method. All of these processes present the problem of reducing the water content of the acetic acid. Acetic acid boils at 118° C. and water at 100° C., but although they do not form an azeotrope, they are far from being an ideal mixture to separate. The separation of water from acetic acid by distillation becomes especially difficult at high concentrations of acetic acid and low concentrations of water.

To address the difficulty in reducing the water content of acetic acid at high acetic acid concentrations, several methods have been developed. One such method is azeotropic distillation as described in U.S. Pat. Nos. 5,980,696, 5,160,412, 2,412,215, 2,317,758, 2,275,802, 2,031,637, G.B. Patent Nos. 623,991, 587,269, and CA Patent Nos. 330,190 and FR 703003. Other methods include extractive distillation, as described in U.S. Pat. No. 5,167,774, and the passing of the mixture through a column of molecular sieves. Some recent methods describe the dehydration of the acetic acid using semi-permeable membranes and pervaporation. However, these methods all have negatives associated with them such as requiring high amounts of energy, not adequately reducing the water content for certain applications, cost, and potentially requiring large capital investment to practice on a commercial scale.

The inventors have found that wet acetic acid can be dehydrated by contacting wet acetic acid with acetyl chloride. The inventors have also found that wet acetic acid may be dehydrated by contacting wet acetic acid with acetic anhydride and with acetyl chloride, hydrogen chloride, or a chlorosilane. The new methods offer the benefits of being able to be conducted in a standard batch reactor or column, reduction of wet acetic acid water content to parts per million levels, and relatively low energy requirements.

BRIEF SUMMARY OF THE INVENTION

The invention pertains to a new method for dehydrating wet acetic acid. Wet acetic acid is dehydrated according to the invention by contacting wet acetic acid with acetyl chloride. Wet acetic acid is also dehydrated by contacting wet acetic acid with acetic anhydride, and with a catalytic effective amount of acetyl chloride, hydrogen chloride, or a chlorosilane.

The following definitions are provided to help describe the invention:

As used herein, "dehydrate" or "dehydrated" is intended to mean to reduce the water content of wet acetic acid but is not intended necessarily to mean that the water content is reduced to zero or no water or that the water is removed.

As used herein, "contact" or "contacted" is intended to mean to bring together in any order such that the compositions and/or materials referenced touch and/or intermingle and is intended to include where one of the materials referenced is formed in situ such as where hydrogen chloride is formed in situ through the reaction between acetyl chloride or a chlorosilane with water.

As used herein, "a catalytic effective amount" is intended to mean an amount sufficient to cause more of the acetic anhydride contacted to react, and to cause the wet acetic acid contacted to be dehydrated further, than if, under similar conditions, the amount was zero.

DETAILED DESCRIPTION OF THE INVENTION

The process of the invention pertains to dehydrating wet acetic acid. As used herein, "wet acetic acid" is intended to mean acetic acid that comprises up to and including 5000 ppm water based upon the weight of the wet acetic acid and that has not been subjected to the process of the invention. Therefore, wet acetic acid according to the invention comprises acetic acid and water. The water content of the wet acetic acid can vary but is reduced when the wet acetic acid is treated according to the process of the present invention. In one embodiment, the wet acetic acid comprises >0 to ≤5000 ppm water; in another embodiment, >0 to <4000 ppm water; in another embodiment, >0 to <3000 ppm water; in another embodiment, >0 to <15000 ppm water. Although the process of the invention may work when larger amounts of water are present in the wet acetic acid, it is generally intended to be used to dehydrate wet acetic acid comprising >0 to ≤5000 ppm water.

In one embodiment of the process of the invention, wet acetic acid is contacted with acetyl chloride. When combined with wet acetic acid, it is believed that the acetyl chloride reacts directly with the water in the wet acetic acid to form acetic acid and hydrogen chloride products. However, there is an equilibrium formed between water and acetyl chloride reactants and the acetic acid and hydrogen chloride products. Thus, although lesser amounts of acetyl chloride will function to dehydrate the wet acetic acid, to maximize dehydration, the acetyl chloride contacted is typically contacted in molar excess to the water from the wet acetic acid contacted to shift the equilibrium to consume more water.

Since the content of the water in the wet acetic acid may vary, the amount of acetyl chloride contacted according to the invention may vary. Greater amounts of water in the wet acetic acid will generally require greater amounts of acetyl chloride. The amount of acetyl chloride contacted can be expressed as the mole % excess compared to the moles of water in the wet acetic acid contacted. Mole % excess refers to the mole % variation from the number of moles of water in the wet acetic acid. To illustrate, if the amount of acetyl chloride is equi-molar to the moles of water, the mole % excess is zero. Or, if there are twice the number of moles of acetyl chloride, the molar excess is 100%, and if there are half the number of moles of acetyl chloride, the molar excess is −(negative) 50%. Therefore, mole % excess is calculated by taking the difference in moles between the acetyl chloride and the water, dividing by the moles of water, and then multiplying by 100. The value is negative when there are fewer moles of acetyl chloride than water and positive when there are more. In one embodiment of the invention, the amount of acetyl chloride contacted is from −75 to 5000 mole % excess of the moles of water from the wet acetic acid; in another embodiment, the amount of acetyl chloride contacted is from −50 to 1000 mole % excess; in another embodiment, the amount of acetyl chloride contacted is from −50 to 800 mole % excess; in another embodiment, the amount of acetyl chloride contacted is from −50 to 500 mole % excess; in another embodiment from −25 to 200 mole % excess; in another embodiment, from −25 to 100 mole % excess; in another embodiment, from >0 to 100 mole % excess. One skilled in the art would know how to determine the mole % water in wet acetic acid and determine the mole % excess of the acetyl chloride to contact. One skilled in the art would also know how to contact the acetyl chloride according to the invention. Acetyl chloride is available commercially, and may be purchased for use in the process of the invention. The in situ preparation of acetyl chloride for use according to the invention is also contemplated. For example, acetyl chloride may be created by the reaction of acetic anhydride and hydrogen chloride, and the resulting mixture comprising acetic acid and acetyl chloride may be combined with the wet acetic acid to affect the wet acetic acid's dehydration.

The temperature at which the wet acetic acid is dehydrated by contacting the wet acetic acid with acetyl chloride may vary. One skilled in the art would know how to vary the temperature of the process of the invention. For example, the ingredients may be heated to the desired temperature and then contacted, or they may be contacted and then heated to the desired temperature. The only limits on the temperature are related to the wet acetic acid dehydration rate and the boiling point of acetic acid. That is, dehydration rate decreases with decreasing process temperature, and if the temperature is too low, the dehydration rate will be so low that the process becomes ineffective. It will be apparent to one of skill in the art that higher temperatures than the boiling point of acetic acid at atmospheric conditions may be used if the process is conducted at pressures above atmospheric pressure. Therefore, the maximum process temperature will depend upon the process pressure. In one embodiment of the invention, the contacting step is conducted at a temperature from ambient to elevated temperature; in another embodiment of the invention, the contacting is conducted at a temperature from 25° C. to 200° C.; in another embodiment, from 25° C. to 125° C.; in another embodiment, at a temperature >25° C. to 125° C.; in another embodiment, from >25° C. to 100° C.; in another embodiment, from 40° C. to 95° C.; in another embodiment, from 50° C. to 85° C.

When acetyl chloride is contacted with wet acetic acid, the time to dehydrate the wet acetic acid will vary. The limits on the time are related to the dehydration rate. As discussed, the process proceeds slower at lower temperature and, therefore, will require more time to dehydrate the wet acetic acid. At temperatures below 25° C., the dehydration rate is so slow as to be practically ineffective. The lower limit for the process time is related to optimization of reaction temperature, pressure, and other factors such as the quantity of acetyl chloride contacted and the desired final water content. Generally, the time to dehydrate wet acetic acid according to the process of the invention decreases with increasing contact temperature. One skilled in the art would know how to vary the process time with other variables such as reaction temperature to optimize dehydration. One skilled in the art would also know how to monitor the water content during the process to determine when the desired dehydration is achieved by, for example, taking reaction samples and measuring the water in the sample by Karl-Fisher titration. In one embodiment, the process of the invention comprising contacting wet acetic acid and acetyl chloride dehydrates the wet acetic acid in >20 minutes; in another embodiment, from 5 minutes to 2 hours; in another embodiment, from 15 minutes to 1 hour; in another embodiment, from 20 minutes to 1 hour.

When acetyl chloride is contacted with wet acetic acid, the pressure at which they are contacted may vary. In one embodiment, the contacting is at a pressure from 0.03 to 1750 kilopascals (KPa); in another embodiment, from 0.03 to 1050 KPa; in another embodiment, from 0.03 to 500 KPa; in another embodiment, from 0.03 to 500 KPa; in another embodiment from 0.03 to 110 KPa; in another embodiment, from 0.03 to 7 KPa; in another embodiment, from 13 to 350 KPa. One skilled in the art would know how to vary the pressure of the reaction.

One skilled in the art would know how to conduct the process of the invention comprising contacting wet acetic acid and acetyl chloride. For example, the process of the invention could be carried out in a plug flow reactor, or in a batch or continuous stirred tank reactor, or in a fixed bed reactor where insoluble hydrogen chloride could be removed from the top.

When wet acetic acid is contacted with acetyl chloride according to the invention, the wet acetic acid is dehydrated. In one embodiment of the invention, the wet acetic acid is dehydrated to produce acetic acid within a range of water content from >0 to 2500 ppm by weight; in another embodiment, from >0 to 800 ppm by weight; in another embodiment, from >0 to 500 ppm; in another embodiment, from >0 to 300 ppm; in another embodiment, from >0 to 200 ppm; in another embodiment, from >0 to 150 ppm; and, in another embodiment, from 50 to 150 ppm. The resulting dehydration of wet acetic acid according to the invention by contacting wet acetic acid with acetyl chloride can also be expressed in terms of the total water conversion. As used herein, "total water conversion" is intended to mean the weight percent of the water in the wet acetic acid that is converted to a chemical compound, or compounds, other than water, such as acetic acid, and is calculated by dividing the difference between the ppm water (based upon the weight of the starting wet acetic acid) before and after subjecting the wet acetic acid to the process of the invention by the starting ppm water of the wet acetic acid and then multiplying by 100 and is expressed in weight percent (%). In one embodiment of the invention, the contacting of acetyl chloride and wet acetic acid results in a total water conversion of from 10 to 99 weight %; in another embodiment, from 20 to 99 weight %; in another embodiment from 20 to 95 weight %; in another embodiment, from 25 to 95 weight %; in another embodiment, from 35 to 95 weight %; and in another embodiment, from 35 to 92 weight %.

In another embodiment of the invention, wet acetic acid is dehydrated by contacting wet acetic acid; acetic anhydride; and hydrogen chloride, acetyl chloride, or a chlorosilane. In one embodiment, wet acetic acid is dehydrated by contacting the wet acetic acid, acetic anhydride, and hydrogen chloride. Not intending to be bound by theory, it is believed that, when wet acetic acid, acetic anhydride, and hydrogen chloride are contacted, the wet acetic acid is dehydrated through a mechanism whereby acetyl chloride is formed in situ by the reaction of hydrogen chloride and acetic anhydride. The acetyl chloride thus formed reacts with the water present from the wet acetic acid to produce acetic acid and hydrogen chloride. This hydrogen chloride can then start the mechanism again by reacting with additional acetic anhydride.

The amount of hydrogen chloride contacted with the wet acetic acid and the acetic anhydride may vary. In one embodiment, the amount of hydrogen chloride contacted is in a catalytic effective amount. Typically, a catalytic effective amount of hydrogen chloride is >5 ppm based upon the weight of wet acetic acid. In another one embodiment, the hydrogen chloride contacted is from 5 ppm to 50,000 ppm based on the weight of the wet acetic acid; in another embodiment from 5 ppm to 10,000 ppm; in another embodiment, from 5 to 5000 ppm; in another embodiment, from 5 to 2000 ppm; in another embodiment, from 25 to 1500 ppm. One skilled in the art would understand how to contact hydrogen chloride with wet acetic acid and acetic anhydride. For example, the hydrogen chloride may be contacted directly with the wet acetic acid and acetic anhydride by introducing hydrogen chloride into the wet acetic acid feed line into the bottom of a plug flow reactor. When directly contacted, the hydrogen chloride is typically anhydrous or nearly anhydrous. If the hydrogen chloride is not anhydrous, additional acetic anhydride is typically added to compensate for and remove the added quantity of water from the non-anhydrous hydrogen chloride. Hydrogen chloride is available commercially for use in directly contacting according to the invention. Hydrogen chloride may also be formed in situ to contact with the wet acetic acid and acetic anhydride according to the invention. For example, hydrogen chloride may be generated in situ by contacting a chlorosilane or acetyl chloride with the wet acetic acid and the acetic anhydride according to the invention.

In one embodiment of the invention, wet acetic acid is dehydrated by contacting wet acetic acid, acetic anhydride, and a catalytic effective amount of acetyl chloride. It is believed that the acetyl chloride affects dehydration of the wet acetic acid through a mechanism where the acetyl chloride reacts with the water present from the wet acetic acid to produce acetic acid and hydrogen chloride. This hydrogen chloride may then, as described above for the direct addition of hydrogen chloride, react with the acetic anhydride to produce acetic acid and acetyl chloride. The acetyl chloride produced may then react with more water to produce acetic acid and additional hydrogen chloride, which can start the mechanism again by reacting with more acetic anhydride. A catalytic effective amount of acetyl chloride is typically >5 ppm based upon the weight of the wet acetic acid. In one embodiment of the invention, the acetyl chloride is contacted with the wet acetic acid and acetic anhydride in an amount from 5 ppm to 50,000 ppm based upon the amount of wet acetic acid contacted; in another embodiment, the acetyl chloride is from 5 ppm to 10,000 ppm based upon the weight of the wet acetic acid; in another embodiment, from 5 to 5000 ppm; in another embodiment, from 5 to 3000 ppm; in another embodiment, from 5 to 2000 ppm; and, in another embodiment, from 25 to 1500 ppm. One skilled in the art would know how to contact acetyl chloride according to the invention to achieve the desired dehydration of wet acetic acid. Acetyl chloride is available commercially.

In one embodiment of the invention, wet acetic acid is dehydrated by contacting wet acetic acid, acetic anhydride and a catalytic effective amount of chlorosilane. Again, not intending to be bound by theory, it is believed that the chlorosilane affects dehydration of the wet acetic acid through a mechanism where the chlorosilane reacts to produce hydrogen chloride. The hydrogen chloride thus produced may react with the acetic anhydride to produce acetic acid and acetyl chloride. The acetyl chloride may then react with water from the wet acetic acid producing acetic acid and more hydrogen chloride, which may react with acetic anhydride the start of the mechanism again. Typically, a catalytic effective amount of chlorosilane is >5 ppm based upon the weight of the wet acetic acid. In one embodiment, the a chlorosilane is contacted at from 5 ppm to 50,000 ppm based upon the weight of the wet acetic acid; in another embodiment, the chlorosilane is contacted at from 5 ppm to 10,000 ppm based upon the weight of the wet acetic acid; in another embodiment, from 5 to 5000 ppm; in another embodiment, from 5 to 3000 ppm; in another embodiment from 5 to 2000 ppm; and, in another embodiment, from 25 to 1500 ppm. One skilled in the art would know how to contact the chlorosilane according to the invention to achieve the desired dehydration of wet acetic acid. Chlorosilanes are available commercially.

Chlorosilanes useful in the present invention are only limited by the requirement that they will react to cause the dehydration of wet acetic acid when contacted with wet acetic acid and acetic anhydride according to the invention. Chlorosilanes that will react to cause wet acetic acid to be dehydrated are believed to be those that produce hydrogen chloride when contacted with the wet acetic acid and acetic anhydride according to the invention. Examples of useful chlorosilanes are monosilanes of formula $R_nSiCl_{4-n}$ wherein each R is independently C1 to C6 alkyl, C1 to C8 cycloalkyl, aryl, aralkyl, alkaryl, or C1 to C6 alkenyl; and, n is an integer from 1 to 3. In one embodiment, the chlorosilanes is tetrachlorosilane, methyltrichlorosilane, dimethyldichlorosilane, trimethylchlorosilane or mixtures thereof. In one embodiment, the chlorosilane is tetrachlorosilane. However, the chlorosilanes useful in the present invention are not limited to monosilanes. For example, the chlorosilane useful in the invention may be a chlorosilane dimer, trimer or greater. Mixtures of chlorosilanes may also be used according to the invention. As long as the chlorosilanes will cause the dehydration of wet acetic acid when contacted with the wet acetic acid and acetic anhydride, the chlorosilanes or mixture of chlorosilanes are useful according to the invention. Chlorosilanes may be purchased commercially or made through the "direct process" in which methyl chloride is reacted with silicon metal in the presence of a copper catalyst or in which hydrogen chloride is reacted directly with silicon metal.

It should be apparent to one of skill in the art that mixtures of hydrogen chloride, a chlorosilane, and acetyl chloride may be contacted with the wet acetic acid and acetic anhydride according to the invention to affect the dehydration of the wet acetic acid. When such mixtures are contacted according to the invention, they will typically be contacted in a catalytic effective amount; in another embodiment, at an amount >5 ppm based upon the weight of wet acetic acid; in another embodiment, from 5 ppm to 50,000 ppm; in another embodiment, from 5 ppm to 10,000 ppm; in another embodiment, from 5 ppm to 5000 ppm; in another embodiment, from 5 ppm to 2000 ppm; and, in another embodiment, from 25 to 1500 ppm.

The amount of acetic anhydride contacted to dehydrate wet acetic acid according to the invention may vary depending upon the amount of water in the wet acetic acid. Greater amounts of water in the wet acetic acid will typically require more acetic anhydride to remove. In theory, the acetic anhydride will react with an equi-molar amount of water; however, it is believed that the reactants will form an equilibrium with the products, and, therefore, a molar excess of acetic anhydride in relation to the amount of water in the acetic acid typically is used to drive the equilibrium in the direction of creating more acetyl chloride and, as a result, removing more water. However, an excess of acetic anhydride is not required to reduce the amount of water in the wet acetic acid. The amount of acetic anhydride contacted may be represented as the mole % excess compared to the moles of water in the wet acetic acid. That is, mole % excess refers to the mole % variation from the moles of water in the wet acetic acid. To illustrate, if the amount of acetic anhydride is equi-molar to the amount of water in the wet acetic acid, the mole % excess is zero. Or, if there are twice the moles of acetic anhydride, the mole % excess is 100%, and if there are half the moles of acetic anhydride, the mole % excess is − (negative) 50%. Therefore, mole % excess is calculated by taking the difference in moles between the acetic anhydride and the water and dividing by the moles of water then multiplying by 100. The value is negative when there are fewer moles of acetic anhydride and positive when there are more. In one embodiment of the invention, the amount of acetic anhydride contacted is from −75 to 300 mole % excess; in another embodiment, the amount of acetic anhydride contacted is from −50 to 250 mole % excess; in another embodiment, from −25 to 200 mole % excess; in another embodiment, from −10 to 200 mole % excess; in another embodiment, from >0 to 200 mole % excess; and, in another embodiment, from >0 to 100 mole % excess. One skilled in the art would know how to determine the moles of water in wet acetic acid and the mole % excess of the acetic anhydride. One skilled in the art would also know how to contact the acetic anhydride according to the invention. Acetic anhydride is available commercially.

The temperature, at which wet acetic acid is dehydrated by contacting the wet acetic acid; acetic anhydride; and hydrogen chloride, a chlorosilane, or acetyl chloride, may vary. Once skilled in the art would know how to vary the temperature of the process of the invention. For example, the ingredients may be heated to the desired temperature and then brought together, or they may be brought together and then heated to the desired temperature. The only limits on the temperature are related to the wet acetic acid dehydration rate and the boiling point of acetic acid. That is, the rate of dehydration decreases with decreasing process temperature, and if the temperature is too low, the process becomes ineffective. If the process temperature is too high, the acetic acid will boil, and the process will again be ineffective. It will be apparent to one of skill in the art that higher temperatures than the boiling point of acetic acid at atmospheric conditions may be used if the process is conducted at pressures above atmospheric pressure. Therefore, the maximum process temperature will depend upon the process pressure. In one embodiment of the invention, the contacting is conducted at a temperature from ambient to elevated temperature; in another embodiment of the invention, the contacting is conducted at a temperature from 25° C. to 200° C.; in another embodiment, from 25° C. to 125° C.; in another embodiment, at a temperature >25° C. to 125° C.; in another embodiment, from >25° C. to 100° C.; in another embodiment, from 40° C. to 95° C.; in another embodiment, at least 20 minutes, and, in another embodiment, from 50° C. to 85° C.

The time to dehydrate the wet acetic acid according to the invention may vary when wet acetic acid is dehydrated by contacting the wet acetic acid; acetic anhydride; and hydrogen chloride, acetyl chloride, or a chlorosilane. The limits on the time are related to the dehydration rate. As discussed, the process proceeds slower at lower temperature and, therefore, will require more time at lower temperatures. At temperatures below 25° C., the dehydration rate is so slow as to be practically ineffective. The lower limit for the process time is related to optimization of reaction temperature, pressure, and other factors such as the desired final water content. Generally, the time to dehydrate the wet acetic acid with the process of the invention decreases with increasing contact temperature. One skilled in the art would know how the process time varies with other variables such as reaction temperature and how to adjust these variables to optimize the dehydration. One skilled in the art would also know how to monitor the water content during the process to determine when the desired reduction in water is achieved by, for example, taking reaction samples and measuring the water in the sample by Karl-Fisher titration. In one embodiment, the process of the invention of contacting wet acetic acid; acetic anhydride; and hydrogen chloride, acetyl chloride, or a chlorosilanes dehydrates the wet acetic acid in >20 minutes; in another embodiment is from 5 minutes to 2 hours; in another embodiment, from 15 minutes to 1 hour; and, in another embodiment, from 20 minutes to 1 hour.

When wet acetic acid is dehydrated by contacting the wet acetic acid; acetic anhydride; and hydrogen chloride, acetyl chloride, or a chlorosilane, the pressure at which they are contacted may vary. In one embodiment, the contacting is at a pressure from 0.03 to 1750 kilopascals (KPa); in another embodiment, from 0.03 to 1050 KPa; in another embodiment, from 0.03 to 500 KPa; in another embodiment, from 0.03 to 500 KPa; in another embodiment, from 0.03 to 110 KPa; in another embodiment, from 0.03 to 7 KPa; in another embodiment, from 13 to 350 KPa. One skilled in the art would know how to vary the pressure of the reacton.

One skilled in the art would know how to conduct the process of the invention comprising contacting wet acetic acid; acetic anhydride; and hydrogen chloride, a chlorosilane, or acetyl chloride. For example, the process of the invention could be carried out in a plug flow reactor, in a batch or continuous stirred tank reactor, or in a fixed bed reactor.

After the wet acetic acid is dehydrated according to the invention by contacting the wet acetic acid; acetic anhydride; and hydrogen chloride, acetyl chloride, or a chlorosilane, the water content of the resulting acetic acid can vary. In one embodiment of the invention, the wet acetic acid is dehydrated to produce acetic acid with a water content from >0 to 2500 ppm by weight; in another embodiment, from >0 to 800 ppm by weight; in another embodiment, from >0 to 500 ppm; in another embodiment, from >0 to 300 ppm; in another embodiment, from >0 to 200 ppm; in another embodiment, from >0 to 150 ppm; and, in another embodiment, from 50 to 150 ppm. The resulting dehydration of wet acetic acid according to the invention by contacting wet acetic acid with acetic anhydride and with a catalytic effective amount of hydrogen chloride, acetyl chloride, or a chlorosilane can also be expressed in terms of the total water conversion. As used herein, "total water conversion" is intended to mean the weight percent of the water in the wet acetic acid that is converted to a chemical compound, or compounds, other than water, such as acetic acid. Total water conversion is calculated by dividing the difference between the ppm water (based upon the weight of the starting wet acetic acid) before and after subjecting the wet acetic acid to the process of the invention by the starting ppm water of the wet acetic acid and then multiplying by 100 and is expressed in weight percent (%). In one embodiment of the invention, the contacting of wet acetic acid with acetic anhydride and with a catalytic effective amount of hydrogen chloride, acetyl chloride, or a chlorosilane results in a total water conversion of from 10 to 99 weight %; in another embodiment, from 20 to 99 weight %; in another embodiment from 20 to 95 weight %; in another embodiment, from 25 to 95 weight %; in another embodiment, from 35 to 95 weight %; and in another embodiment, from 35 to 92 weight %.

The dehydrated acetic acid produced according to the invention finds use in the production of materials with high sensitivity to moisture. For example, low amounts of moisture are desired in the production of acetoxy silanes used to form low moisture curing silicon elastomers.

EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute modes for its practice. However, those of skill in the art should, in light of the present disclosure, appreciate that many changes can be made in the specific embodiments which are disclosed and still obtain a like or similar result without departing from the spirit and scope of the invention. Unless otherwise indicated, all percentages are in weight % (wt. %). The ppm water was determined by Karl-Fisher titration of the water present or by mass balance calculations based upon the amount of acetyl chloride or acetic anhydride present in the product as determined by gas chromatography (GC). When the unit 'parts per million' (ppm) are used in the example, it is based on weight.

Example 1

Wet acetic acid, containing 560 parts per million (ppm) water, acetic anhydride in 24 mole % excess, and hydrogen chloride, at 0.115 weight % of the wet acetic acid, were introduced into a plug flow reactor that was heated to 75° C. The residence time of the materials in the reactor was 40 minutes. The resulting product contained 151 ppm water, which equates to a total water conversion of 73 weight %.

Example 2

Wet acetic acid, containing 838 parts per million (ppm) water, acetic anhydride at a 25 mole % excess, and hydrogen chloride, at 0.25 weight % of the wet acetic acid, were introduced into a plug flow reactor that was heated to 75° C. The residence time of the materials in the reactor was 39 minutes. The resulting product contained 251 ppm water, which equates to a total water conversion of 70 weight %.

Example 3

Wet acetic acid, containing 2419 parts per million (ppm) water, acetic anhydride at a 50 mole % excess to the water in the wet acetic acid, and hydrogen chloride, at 0.115 weight % of the wet acetic acid, were introduced into a plug flow reactor that was heated to 75° C. The residence time of the materials in the reactor was 40 minutes. The resulting product contained 226 ppm water, which equates to a total water conversion of 89 weight %.

Example 4

Wet acetic acid, acetic anhydride, and hydrogen chloride were introduced into a glass packed column varying the temperature, flow rate of the hydrogen chloride, and the amount of acetic anhydride. The starting ppm water in the acetic acid and the resulting water in the product were measured by Karl-Fisher titration. The residence time in the column was 30 minutes and the flow rate of acetic acid was 6.5 milliliters/minute. The results are in Table 1.

TABLE 1

Results of dehydration at varying temperatures, hydrogen chloride flow rates, wet acetic acid water contents, and ratios of acetic anhydride to the water content of the wet acetic acid.

| Run Number | Temp. (° C.) | HCl Flow Rate (ml/min) | Acetic Anhydride Excess (%) | Wet Acetic Acid Water (ppm) | Product Water Content (ppm) |
| --- | --- | --- | --- | --- | --- |
| 1* | 70 | 0 | −1 | 545 | 491 |
| 2 | 70 | <1 | −4 | 545 | 145 |
| 3 | 70 | <1 | −50 | 1050 | 486 |
| 4* | 70 | 0 | None added | 494 | 475 |
| 5* | 70 | 50 | None added | 494 | 492 |
| 6 | 70 | 1.5 | 50 | 1000 | 89 |
| 7 | 70 | 5 | 10 | 675 | 185 |
| 8 | 25 | 6 | −50 | 541 | 505 |
| 9 | 40 | 6 | −50 | 541 | 390 |
| 10 | 55 | 6 | −50 | 541 | 347 |

*Runs 1, 4, and 5 are comparative examples.

Example 5

Wet acetic acid containing 850 ppm of water and acetic anhydride at 200 mole % were added to a batch reactor, heated to and then held at 35° C. for 38 minutes while anhydrous hydrogen chloride gas was bubbled into the reaction mixture. A sample was analyzed by GC for acetyl chloride and acetic anhydride and the amount of water calculated by mass balance calculations to be 170 ppm of water based upon the starting wet acetic acid weight which equates to a total water conversion of 80 weight %.

Example 6

Comparative

Wet acetic acid containing 4600 ppm water was combined with acetic anhydride in 0 mole % excess at 25° C. and mixed for 120 minutes. After 120 minutes, the reactants were sampled and the amount of acetic anhydride was tested by GC, and the product calculated to contain 4400 ppm water. The mixture was then heated to, and held at, 50° C. for 2 hrs. A sample was again taken and determined to contain 4250 ppm of water based on the starting wet acetic acid. The product was then heated at 50° C. for 48 hours resulting in a product which contained 2100 ppm water based upon the starting wet acetic acid.

Example 7

To the initial 0 mole % excess acetic acid and acetic anhydride mixture described in Example 6, was added 400 ppm, based upon the weight of the wet acetic acid, acetyl chloride. This reaction mixture was held at 25° C. for 120 minutes. The resulting product contained 2000 ppm water, which equates to a total water conversion of 56 weight %.

Example 8

A batch reactor with an electric agitator and temperature control was charged with wet acetic acid containing 850 ppm of water and heated to 50° C. Acetyl chloride was added to the reactor in 100% molar excess of the water in the wet acetic acid and the reactants heated at 50° C. for 28 minutes. The resulting product contained 85 ppm water, which equates to a total water conversion of 90 weight %.

Example 9

Wet acetic acid and acetyl chloride were introduced into a batch reactor varying the amount of acetyl chloride in proportion to the water in the wet acetic acid, the residence time, and the temperature in the reactor. The quantity of acetic anhydride and acetyl chloride in the product were determined by gas chromatography (GC), and the conversion of water from the wet acetic acid was then determined based on the mass balance of acetyl chloride and acetic anhydride in the system at a given time. The results are listed in Table 2 below. The acetyl chloride introduced is expressed in terms of excess in relation to the water from the wet acetic acid with 0% being an equi-molar amount of acetyl chloride and water.

TABLE 2

Results of plug flow experiments with acetyl chloride and wet acetic acid.

| Run No. | Temp. (° C.) | Excess Acetyl Chloride (%) | Wet Acetic Acid Initial Water Content (ppm) | Total Water Conversion (weight %) | Residence Time (min.) |
|---|---|---|---|---|---|
| 1 | 50 | 100 | 850 | 90 | 28 |
| 2 | 40 | 100 | 850 | 60 | 40 |
| 3 | 25 | 100 | 850 | 35 | 100 |

That which is claimed is:

1. A process for dehydrating wet acetic acid, comprising contacting wet acetic acid and acetyl chloride wherein the contacting results in a total water conversion of from 10 to 99 weight % of the water in the wet acetic acid.

2. The process of claim 1 wherein the contacting is at a temperature from 25° C. to 200° C.

3. The process of claim 2 wherein the temperature is from 50° C. to 85° C.

4. The process of claim 1 where in the wet acetic acid comprises 0.01 to ≤0.15 weight % water based upon the weight of the wet acetic acid.

5. The process of claim 1, wherein the acetyl chloride is from −75 to 5000 mole % excess compared to the water.

6. The process of claim 5 wherein the acetyl chloride is from −25 to 100 mole % excess compared to the water.

7. The process of claim 1 wherein the wet acetic acid comprises from >0 to 50,000 ppm water based on the weight of the acetic acid.

8. A process for dehydrating wet acetic acid, comprising: contacting wet acetic acid, acetic anhydride, and a catalytic effective amount of i) hydrogen chloride, ii) a chlorosilane, iii) acetyl chloride, or iv) mixtures of i), ii) and iii), wherein the contacting results in a total water conversion of from 10 to 99 weight % of the water in the wet acetic acid, and wherein the contacting results in in situ production of acetyl chloride.

9. The process of claim 8 wherein the contacting is at a temperature from 25° C. to 200° C.

10. The process of claim 9 wherein the temperature is from 50° C. to 85° C.

11. The process of claim 8 wherein a catalytic effective amount of i) hydrogen chloride is contacted with the wet acetic acid and the acetic anhydride.

12. The process of claim 11 wherein the i) hydrogen chloride is formed in situ from the contacting of ii) or iii) with the acetic anhydride and the wet acetic acid.

13. The process of claim 8 wherein the catalytic effective amount is from 5 ppm to 50,000 ppm based on the weight of the wet acetic acid.

14. The process of claim 13 wherein the catalytic effective amount is from 5 to 2000 ppm based upon the weight of the wet acetic acid contacted.

15. The process of claim 8 where in the wet acetic acid comprises >0 to 50,000 ppm water based upon the weight of the wet acetic acid.

16. The process of claim 15 wherein the wet acetic acid comprises >0 to 2000 ppm water based upon the weight of the wet acetic acid.

17. The process of claim 8 wherein the acetic anhydride is in from −75 to 300 mole % excess to the water in the wet acetic acid.

18. The process of claim 17 wherein the acetic anhydride is in from −25 to 100 mole % excess to the water in the wet acetic acid.

19. A process of dehydrating wet acetic acid, comprising: contacting wet acetic acid comprising >0 to 2000 ppm water based on the weight of wet acetic acid; acetic anhydride in −25 to 100 mole % excess compared to the water in the wet acetic acid; and a catalytic effective amount of hydrogen chloride, a chlorosilane, or acetyl chloride at a temperature from 50 to 85° C., wherein the contacting results in a total water conversion of from 20 to 95 weight % of the water in the wet acetic acid, and wherein the contacting results in in situ production of acetyl chloride.

* * * * *